United States Patent
Fevola (10) Patent No.: US 8,227,393 B2
(45) Date of Patent: Jul. 24, 2012

(54) COMPOSITIONS COMPRISING A POLYGLYCERYL NONIONIC SURFACTANT AND A ZWITTERIONIC SURFACTANT

(75) Inventor: Michael J. Fevola, Belle Mead, NJ (US)

(73) Assignee: Johnson & Johnson Consumer Companies, Inc. NJ (US)

( * ) Notice: Subject to any disclaimer, the term of this patent is extended or adjusted under 35 U.S.C. 154(b) by 44 days.

(21) Appl. No.: 12/974,268

(22) Filed: Dec. 21, 2010

(65) Prior Publication Data
US 2012/0157365 A1 Jun. 21, 2012

(51) Int. Cl.
C11D 1/94 (2006.01)

(52) U.S. Cl. ........ 510/123; 510/119; 510/125; 510/127; 510/130; 510/155; 510/156; 510/426; 510/427

(58) Field of Classification Search ........... 510/119, 510/123, 125, 127, 130, 155, 156, 426, 427
See application file for complete search history.

(56) References Cited

U.S. PATENT DOCUMENTS

| | | | |
|---|---|---|---|
| 2,999,069 A | 9/1961 | Masci et al. | |
| 3,055,836 A | 9/1962 | Masci et al. | |
| 3,950,417 A | 4/1976 | Verdicchio et al. | |
| 4,177,171 A | 12/1979 | Walts | |
| 5,478,490 A * | 12/1995 | Russo et al. | 510/122 |
| 6,762,159 B2 | 7/2004 | Ishitobi | |
| 2003/0211066 A1 | 11/2003 | Scholz | |
| 2011/0319307 A1 * | 12/2011 | Gunn et al. | 510/130 |

FOREIGN PATENT DOCUMENTS

| | | |
|---|---|---|
| EP | 0499700 A1 | 8/1992 |
| EP | 1674132 A1 | 6/2006 |
| JP | 1999148099 | 6/1999 |

OTHER PUBLICATIONS

Löffler, H. and Happle, R., *Contact Dermatitis*, 2003, 48, 26-32.
Mehling, A., et al., *Food and Chemical Toxicology*, 2007, 45, 747-758.
European Search Report dated Apr. 4, 2012 for correspondeing EP patent application No. 11194609.1.

* cited by examiner

Primary Examiner — Charles Boyer (57) ABSTRACT

Provided are compositions comprising a polyglyceryl nonionic surfactant, a zwitterionic surfactant, an organic acid preservative, a non-sulfate anionic surfactant and water, wherein the composition is substantially free of ethoxylated materials and has a pH of about 5.4 or less, and uses thereof. Also provided are compositions comprising a polyglyceryl nonionic surfactant, a zwitterionic surfactant, an organic acid preservative, and water, wherein the composition is substantially free of ethoxylated materials, substantially free of sulfated anionic surfactants, and has a pH of about 5.4 or less, and uses thereof.

21 Claims, 1 Drawing Sheet

COMPOSITIONS COMPRISING A POLYGLYCERYL NONIONIC SURFACTANT AND A ZWITTERIONIC SURFACTANT

FIELD OF INVENTION

The present invention relates to compositions comprising polyglyceryl nonionic surfactants. More specifically, in preferred embodiments, it relates to mild cleansing compositions comprising polyglyceryl nonionic surfactants.

DESCRIPTION OF RELATED ART

Applicants have recognized the desirability of developing clear and mild cleansers having a relatively low pH, e.g. of about 5.4 or less, that are also substantially free of ethoxylated (EO) materials. While certain EO-free cleansers have been made previously at higher pH, for example, as described in U.S. Pat. No. 5,478,490 issued to Russo et al, applicants have recognized that a relatively low pH can have significant negative effects on the clarity, as well as the viscosity and other properties associated with consumer appeal of a cleanser.

Accordingly, applicants have recognized the need to develop cleansers at low pH that exhibit clarity, mildness, and/or desirable viscosity for consumer use.

SUMMARY OF THE INVENTION

According to one aspect, the present invention provides compositions comprising a polyglyceryl nonionic surfactant, a zwitterionic surfactant, an organic acid preservative, a non-sulfate anionic surfactant and water, wherein the composition is substantially free of ethoxylated materials and has a pH of about 5.4 or less.

According to another aspect, the present invention provides compositions comprising a polyglyceryl nonionic surfactant, a zwitterionic surfactant, an organic acid preservative, and water, wherein the composition is substantially free of ethoxylated materials, substantially free of sulfated anionic surfactants, and has a pH of about 5.4 or less.

According to another aspect, the present invention provides methods of cleansing the skin comprising applying to skin a composition of the present invention.

DESCRIPTION OF PREFERRED EMBODIMENTS

Applicants have discovered that the compositions of the present invention overcome the disadvantages of the prior art and provide compositions that exhibit an unexpected combination of desirable properties as compared to the prior art. In particular, embodiments of the present invention provide compositions having one or more properties including clarity, good viscosity, and/or foaming action, while maintaining excellent mildness to the skin and eyes without the aid of ethoxylated surfactants.

More specifically, applicants have tested the clarity associated with compositions of the present invention as compared to comparable compositions comprising sulfated anionic surfactants and discovered unexpectedly that the compositions of the present invention exhibit significant benefits in clarity over the other compositions. For example, as shown in the Examples, compositions of the present invention tended to exhibit high clarity and low turbidity.

All percentages listed in this specification are percentages by weight, unless otherwise specifically mentioned.

As used herein, the term "substantially free of ethoxylated materials" means a composition that comprises less than 1% by weight of total ethoxylated materials. In preferred embodiments, compositions that are substantially free of ethoxylated materials comprise less than 0.5%, more preferably less than 0.1%, and even more preferable are free of, ethoxylated materials.

As used herein, the term "ethoxylated material" means a material comprising one or more moieties derived from or prepared by the ring-opening oligomerization or polymerization of ethylene oxide and/or comprising one or more oxyethylene (—$CH_2CH_2O$—) moieties. Examples of ethoxylated materials include, but are not limited to, ethoxylated surfactants, emulsifiers, solubilizers, rheology modifiers, conditioning agents, preservatives, and the like, such as, for example anionic surfactants: polyoxyethylene alkyl ether sulfates (a.k.a. alkyl ether sulfates), polyoxyethylene alkyl ether carboxylates (a.k.a. alkyl ether carboxylates), polyoxyethylene alkyl ether sulfosuccinate esters; nonionic surfactants, emulsifiers, and solubilizers: polyoxyethylene alkyl ethers and esters, polysorbates, ethoxylated sorbitan fatty acid esters, ethoxylated glyceryl fatty acid esters, poloxamers; rheology modifiers: polyoxyethylene esters (e.g. PEG-150 Distearate), ethyoxylated alkyl glucoside esters (e.g. PEG-120 Methyl Glucose Trioleate), acrylic copolymers with ethoxylated associative macromonomers (e.g. Acrylates/Steareth-20 Methacrylate Copolymer), ethoxylated cellulose ethers (e.g. Hydroxyethylcellulose); conditioning agents: ethoxylated polyquaterniums (e.g. Polyquaternium-10); and the like.

As used herein, the term "glyceryl repeat unit" refers to a repeat unit that is a structural derivative of glycerol ($C_3H_8O_3$), such as repeat units corresponding to dehydrated glycerol ($C_3H_6O_2$). Examples of glyceryl repeat units include:

(a) linear-1,4 ($L_{1,4}$) repeat units of the formula:

(b) linear-1,3 ($L_{1,3}$) PG repeat units of the formula:

(c) dendritic (D) PG repeat units, which lead to branched and cyclic PGs, of the formula:

(d) terminal-1,2 ($T_{1,2}$) units (shown attached to a polyglyceryl moiety PG) of the formula:

and
and (e) terminal-1,3 ($T_{1,3}$) units (shown attached to a polyglyceryl moiety PG) of the formula:

As used herein, a "polyglyceryl moiety" means a linear, branched, and/or cyclic polyether moiety comprising two or more glyceryl repeat units. Polyglyceryl moieties may be derived via any of a variety of synthetic routes, including but not limited to condensation polymerization of glycerol, ring-opening polymerization of glycerol carbonate, and ring-opening polymerization of glycidol. In certain embodiments, polyglyceryl moieties comprise homopolyethers wherein all of the repeat units are glyceryl repeat units. In certain other embodiments, the polyglyceryl moieties are copolyethers, that is, they comprise both glyceryl repeat units and additional polyether repeat units that are not glyceryl repeat units. For example, glycerol may be copolymerized with 1,3-propanediol to yield a copolyether comprising both glyceryl repeat units described above and oxypropylene repeat units of the formula:

In the formulae herein and above, a polyglyceryl moiety is represented by "PG".

As used herein, the term "polyglyceryl nonionic surfactant" means an amphiphilic molecule comprising one or more nonionic hydrophilic segments comprised of a polyglyceryl moiety and one or more hydrophobic moieties. Examples of polyglyceryl nonionic surfactants include, but are not limited to, polyglyceryl esters (PGEs), such as polyglyceryl-10 laurate where PG=polyglyceryl moiety comprising ten (10) glyceryl repeat units, and R=$C_{11}H_{23}$:

as well as, polyglyceryl-10 caprylate/caprate, polyglyceryl-10 cocoate, polyglyceryl-10 myristate, polyglyceryl-10 palmitate, polyglyceryl-10 oleate, polyglyceryl-12 laurate, and the like. PGEs of the present invention may include polyglyceryl moieties bearing multiple ester substitutions (i.e. the PGEs may be monoesters, diesters, triesters, etc.). Other polyglyceryl nonionic surfactants include polyglyceryl ethers, such as polyglyceryl-10 lauryl ether, where PG=polyglyceryl moiety comprising 10 glyceryl repeat units, and R=$C_{12}H_{25}$:

and the like. Still other polyglyceryl nonionic surfactants include polyglyceryl sorbitan fatty acid esters, such as polyglyceryl-20 sorbitan laurate, where PG=polyglycerol, the sum of all PG RUs=20, and R=$C_{11}H_{23}$. (see Bevinakatti, et al. WO 2009016375, assigned to Croda International PLC)

Any suitable polyglyceryl nonionic surfactants may be used in the compositions of the present invention. In certain preferred embodiments, the polyglyceryl nonionic surfactants are selected from the group consisting of polyglyceryl esters, polyglyceryl ethers, polyglyceryl sorbitan fatty acid esters, combinations of two or more thereof and the like. In certain more preferred embodiments, the polyglyceryl nonionic surfactants are selected from the group consisting of polyglyceryl esters, polyglyceryl ethers, and combinations of two or more thereof. In certain other preferred embodiments, the compositions of the present invention comprise one or more polyglyceryl nonionic surfactants selected from the group consisting of: polyglyceryl-4 caprylate/caprate, polyglyceryl-5 caprylate/caprate, polyglyceryl-6 caprylate/caprate, polyglyceryl-7 caprylate/caprate, polyglyceryl-8 caprylate/caprate, polyglyceryl-9 caprylate/caprate, polyglyceryl-10 caprylate/caprate, polyglyceryl-4 caprate, polyglyceryl-5 caprate, polyglyceryl-6 caprate, polyglyceryl-7 caprate, polyglyceryl-8 caprate, polyglyceryl-9 caprate, polyglyceryl-10 caprate, polyglyceryl-4 laurate, polyglyceryl-5 laurate, polyglyceryl-6 laurate, polyglyceryl-7 laurate, polyglyceryl-8 laurate, polyglyceryl-9 laurate, polyglyceryl-10 laurate, polyglyceryl-6 cocoate, polyglyceryl-7 cocoate, polyglyceryl-8 cocoate, polyglyceryl-9 cocoate, polyglyceryl-10 cocoate, polyglyceryl-11 cocoate, polyglyceryl-12 cocoate, polyglyceryl-6 myristate, polyglyceryl-7 myristate, polyglyceryl-8 myristate, polyglyceryl-9 myristate, polyglyceryl-10 myristate, polyglyceryl-11 myristate, polyglyceryl-12 myristate, polyglyceryl-10 oleate, polyglyceryl-11 oleate, polyglyceryl-12 oleate, polyglyceryl-10 stearate, polyglyceryl-11 stearate, polyglyceryl-12 stearate, and combinations of two or more thereof.

In preferred embodiments, the polyglyceryl nonionic surfactants used in the present invention have a total combined glyceryl degree of polymerization (DP) (i.e. total of all glyceryl repeat units in a given molecule) of from about 4 to about 40 repeat units. In certain more preferred embodiments, the polyglyceryl nonionic surfactants have a DP of from about 6 to about 30, more preferably from about 6 to about 20, more preferably, from about 6 to about 15, and more preferably from about 6 to about 12 glyceryl repeat units.

Any suitable amount of polyglyceryl nonionic surfactant may be used in the compositions of the present invention. In certain embodiments, the compositions comprise from greater than zero to about 25% by weight of polyglyceryl nonionic surfactant. In certain preferred embodiments, the compositions comprise from about 0.05 wt % to about 20 wt %, more preferably from about 0.1 wt % to about 15 wt %, and even more preferably from about 0.2 wt % to about 10 wt %, and still more preferably from about 0.25 wt % to about 5 wt % of total polyglyceryl nonionic surfactant.

As used herein the term "zwitterionic surfactant" refers to an amphiphilic molecule comprising a hydrophobic group and one or more hydrophilic groups comprising two moieties of opposite formal charges or capable of bearing opposite formal charges (as a function of acid-base properties and solution pH). Any suitable zwitteronic surfactant may be used in the present invention. Examples of suitable zwitteronic surfactants include:

Alkyl betaines of the formula:

where r=c$_6$-c$_{24}$ alkyl (saturated or unsaturated) or mixtures thereof examples include cocobetaine (R=coco alkyl), lauryl betaine (R=lauryl, C$_{12}$H$_{25}$), and oleyl betaine (R=oleyl, C$_{18}$H$_{35}$).

Alkyl hydroxysultaines of the formula:

where R=C$_6$-C$_{24}$ alkyl (saturated or unsaturated) or mixture thereof. Examples include coco-hydroxysultaine (R=coco alkyl) and lauryl hydroxysultaine (R=lauryl, C$_{12}$H$_{25}$).

Alkyl sultaines of the formula:

where R=C$_6$-C$_{24}$ alkyl (saturated or unsaturated) or mixture thereof. Examples include lauryl sultaine (R=lauryl, C$_{12}$H$_{25}$) and coco-sultaine (R=coco alkyl).

Alkylamidoalkyl betaines of the formula:

where RCO=C$_6$-C$_{24}$ acyl (saturated or unsaturated) or mixtures thereof and x=1-4. Examples include cocamidoethyl betaine (RCO=coco acyl, x=2), cocamidopropyl betaine (RCO=coco acyl, x=3), lauramidopropyl betaine (RCO=lauroyl, and x=3), myristamidopropyl betaine (RCO=myristoyl, and x=3), soyamidopropyl betaine (R=soy acyl, x=3), and oleamidopropyl betaine (RCO=oleoyl, and x=3).

Alkylamidoalkyl hydroxysultaines of the formula:

where RCO=C$_6$-C$_{24}$ acyl (saturated or unsaturated) or mixtures thereof. Examples include cocamidopropyl hydroxysultaine (RCO=coco acyl, x=3), lauramidopropyl hydroxysultaine (RCO=lauroyl, and x=3), myristamidopropyl hydroxysultaine (RCO=myristoyl, and x=3), and oleamidopropyl hydroxysultaine (RCO=oleoyl, and x=3).

Alkylamidoalkyl sultaines of the formula:

where RCO=C$_6$-C$_{24}$ acyl (saturated or unsaturated) or mixtures thereof. Examples include cocamidopropyl sultaine (RCO=coco acyl, x=3), lauramidopropyl sultaine (RCO=lauroyl, and x=3), myristamidopropyl sultaine (RCO=myristoyl, and x=3), soyamidopropyl betaine (RCO=soy acyl, x=3), and oleamidopropyl betaine (RCO=oleoyl, and x=3).

Alkyl phosphobetaines of the formula:

where R=C$_6$-C$_{24}$ alkyl (saturated or unsaturated) or mixtures thereof and M$^+$=monovalent cation, such as sodium coco PG-dimonium chloride phosphate, where R=coco alkyl and M$^+$=Na$^+$.

Phospholipids of the formula:

where R=C$_6$-C$_{24}$ alkyl (saturated or unsaturated) or mixtures thereof, x=1-3 or mixtures thereof, x+y=3, z=x, a=0 to 2, B=O$^-$ or OM, A=Anion, and M=Cation (refer to U.S. Pat. Nos. 5,215,976; 5,286,719; 5,648,348; and 5,650,402), such as sodium coco PG-dimonium chloride phosphate, where R=coco alkyl, x=2, B=O$^-$, y=1, z=1, A=Cl$^-$, a=1, and M=Na$^+$.

Phospholipids of the formula:

$zA + aM$ where RCO=$C_6$-$C_{24}$ acyl (saturated or unsaturated) or mixtures thereof, n=1-4, x=1-3 or mixtures thereof, x+y=3, z=x, a=0 to 2, B=$O^-$ or OM, A=anion, and M=cation (refer to U.S. Pat. Nos. 5,215,976; 5,286,719; 5,648,348; and 5,650,402). Examples include cocamidopropyl PG-dimonium chloride phosphate (RCO=coco acyl, n=3, x=3, z=3, A=$Cl^-$, B and M are absent, y=0, and a=0) and myristamidopropyl PG-dimonium chloride phosphate (RCO=myristoyl, n=3, x=3, z=3, A=$Cl^-$, B and M are absent, y=0, and a=0).

Amphoacetates of the formula:

where RCO=$C_6$-$C_{24}$ acyl (saturated or unsaturated) or mixtures thereof and $M^+$=monovalent cation. Examples include sodium lauroamphoacetate (RCO=lauroyl and $M^+$=$Na^+$) and sodium cocoamphoacetate (RCO=coco acyl and $M^+$=$Na^+$).

Amphodiacetates of the formula:

where RCO=$C_6$-$C_{24}$ acyl (saturated or unsaturated) or mixtures thereof and $M^+$=monovalent cation. Examples include disodium lauroamphodiacetate (RCO=lauroyl and M=$Na^+$) and disodium cocoamphodiacetate (RCO=coco acyl and M=$Na^+$).

Amphopropionates of the formula:

where RCO=$C_6$-$C_{24}$ acyl (saturated or unsaturated) or mixtures thereof and $M^+$=monovalent cation. Examples include sodium lauroamphopropionate (RCO=lauroyl and $M^+$=$Na^+$) and sodium cocoamphopropionate (RCO=coco acyl and $M^+$=$Na^+$).

Amphodipropionates of the formula:

where RCO=$C_6$-$C_{24}$ acyl (saturated or unsaturated) or mixtures thereof and $M^+$=monovalent cation. Examples include disodium lauroamphodipropionate (RCO=lauroyl and $M^+$=$Na^+$) and disodium cocoamphodipropionate (RCO=coco acyl and $M^+$=$Na^+$).

Amphohydroxypropylsulfonates of the formula:

where RCO=$C_6$-$C_{24}$ acyl (saturated or unsaturated) or mixtures thereof and $M^+$=monovalent cation, such as sodium lauroamphohydroxypropylsulfonate (RCO=lauroyl and $M^+$=$Na^+$) and sodium cocoamphohydroxypropylsulfonate (RCO=coco acyl and $M^+$=$Na^+$).

Amphohydroxyalkylphosphates of the formula:

where RCO=$C_6$-$C_{24}$ acyl (saturated or unsaturated) or mixtures thereof and $M^+$=monovalent cation, such as sodium lauroampho PG-acetate phosphate (RCO=lauroyl and $M^+$=$Na^+$).

Alkyl amine oxides of the formula:

where R=$C_6$-$C_{24}$ alkyl (saturated or unsaturated) or mixtures thereof. Examples include cocamine oxide (R=coco alkyl) and lauramine oxide (RCO=lauryl).

Alkylamidoalkyl amine oxides of the formula:

where RCO=$C_6$-$C_{24}$ acyl (saturated or unsaturated) or mixtures thereof and x=1-4. Examples include cocamidopropylamine oxide (RCO=coco acyl, x=3) and lauramidopropylamine oxide (RCO=lauroyl, x=3); and combinations of two or more thereof, and the like. According to certain preferred embodiments, the zwitterionic surfactant is selected from the group consisting of alkyl betaines, alkyl hydroxysultaines, alkylamidoalkyl betaines, alkylamidoalkyl hydroxysultaines, amphohydroxypropylsulfonates, and combinations of two or more thereof.

Any suitable amount of zwitterionic surfactant may be used in the compositions of the present invention. In certain embodiments, the compositions comprise from greater than zero to about 30% by weight of zwitterionic surfactant. In certain preferred embodiments, the compositions comprise from about 0.5 wt % to about 25 wt %, more preferable from about 1.0 wt % to about 20 wt %, still more preferably from about 2.0 wt % to about 15 wt %, and even more preferably from about 2.5 wt % to about 12.5 wt % of total zwitterionic surfactant.

Any suitable ratio of wt % polyglyceryl nonionic surfactant to wt % zwitterionic surfactant may be used in accord with the present invention. In certain embodiments the ratio of wt % polyglyceryl nonionic surfactant:wt % zwitterionic surfactant is from about 0.01:1 to about 5:1. In certain preferred embodiments, the wt % polyglyceryl nonionic surfactant:wt % zwitterionic surfactant ratio is from about 0.025:1 to about 4:1, more preferably from about 0.05:1 to about 3:1. In certain more preferred embodiments, the wt % polyglyceryl nonionic surfactant: wt % zwitterionic surfactant ratio is from about 0.06:1 to about 2.5:1, and more preferably from about 0.01:1 to about 2:1.

Any organic acids that comprise at least one carboxylic acid moiety and are capable of preserving a composition of the present invention against microbial contamination may be used in accord with the present invention as an organic acid preservative. Examples of suitable organic acids include benzoic acid and alkali metal and ammonium salts thereof (e.g. sodium benzoate and the like), sorbic acid and alkali metal and ammonium salts thereof (e.g. potassium sorbate and the like), p-anisic acid and alkali metal and ammonium salts thereof, salicylic acid and alkali metal and ammonium salts thereof, and the like. in certain preferred embodiments, the organic acid preservative comprises benzoic acid/sodium benzoate, sorbic acid/potassium sorbate, or combinations thereof.

To ensure that the organic acid is present in its active protonated form, the final pH of the composition is preferably kept at about 5.4 or less, more preferably below 5.4, more preferably below 5.2, more preferably below 5.0, and most preferably below 4.9. The pH of the composition may be adjusted as low as 3.0 provided that formula stability and performance (e.g. foaming) are not negatively affected. The pH of the composition may be adjusted to the appropriate acidic value using any cosmetically acceptable organic or inorganic acid, such as citric acid, acetic acid, glycolic acid, lactic acid, malic acid, tartaric acid, hydrochloric acid, combinations of two or more thereof or the like.

Any suitable amount of organic acid preservative may be used in the compositions of the present invention. In certain embodiments, the compositions comprise from greater than zero to about 5% by weight of organic acid preservative. In certain preferred embodiments, the compositions comprise from about 0.05 wt % to about 3 wt %, more preferably from about 0.1 wt % to about 2.5 wt %, and even more preferably from about 0.25 wt % to about 2 wt % of organic acid preservative.

In certain embodiments, the compositions of the present invention comprise a non-sulfate anionic surfactant selected from the group consisting of acyl aspartates, acyl glutamates, acyl isethionates, acyl taurates, alkyl sulfoacetates, alpha-sulfo fatty acid esters, alpha-sulfo fatty acid salts, alpha-olefin sulfonates, alkyl sulfonates, alkyl phosphates, anionic derivatives of alkyl polyglucosides, and combinations of two or more thereof. Examples of such suitable non-sulfate anionic surfactants include, but are not limited to:

Alpha olefin sulfonates prepared by sulfonation of long chain alpha olefins. Alpha olefin sulfonates consist of mixtures of alkene sulfonates, where $R=C_4-C_{18}$ alkyl or mixtures thereof and $M^+$=monovalent cation, and hydroxyalkyl sulfonates, where $R=C_4-C_{18}$ alkyl or mixtures thereof and $M^+$=monovalent cation. Examples include sodium C12-14 olefin sulfonate ($R=C_8-C_{10}$ alkyl, $M^+=Na^+$) and sodium C14-16 olefin sulfonate ($R=C_{10}-C_{12}$ alkyl, $M^+=Na^+$);

Alkyl Sulfonates:

where $R=C_6-C_{24}$ alkyl (linear or branched, saturated or unsaturated) or mixtures thereof and $M^+$=monovalent cation. Examples include sodium C13-17 alkane sulfonate ($R=C_{13}-C_{17}$ alkyl, $M^+=Na^+$) and sodium C14-17 alkyl sec sulfonate ($R=C_{14}-C_{17}$ alkyl, $M^+=Na^+$);

(c) Alkyl glyceryl ether sulfonates:

where $R=C_6-C_{24}$ alkyl (linear or branched, saturated or unsaturated) or mixtures thereof and $M^+$=monovalent cation, such as sodium cocoglyceryl ether sulfonate (R=coco alkyl, $M^+=Na^+$);

α-Sulfo Fatty Acid Esters

Where $R=C_4-C_{16}$ alkyl (linear or branched, saturated or unsaturated) or mixtures thereof, $R'=C_1-C_4$ alkyl, and $M^+$=monovalent cation, such as sodium methyl 2-sulfolaurate ($R=C_{10}H_{21}$, R'=methyl, $CH_3$, and $M^+=Na^+$);

α-Sulfo Fatty Acid Salts

Where R=$C_4$-$C_{16}$ alkyl (linear or branched, saturated or unsaturated) or mixtures thereof, $M^+$=monovalent cation, such as disodium 2-sulfolaurate (R=$C_{10}H_{21}$, $M^+$=$Na^+$);

Alkyl Sulfoacetates

Where R=$C_6$-$C_{18}$ alkyl (linear or branched, saturated or unsaturated) or mixtures thereof, $M^+$=monovalent cation, such as sodium lauryl sulfoacetate (R=lauryl, $C_{12}H_{25}$, $M^+$=$Na^+$).

Acyl Isethionates

Where RCO=$C_6$-$C_{20}$ acyl (linear or branched, saturated or unsaturated) or mixtures thereof, R'=H or $CH_3$, $M^+$=monovalent cation, such as sodium cocoyl isethionate (RCO=coco acyl, R'=H, $M^+$=$Na^+$) and sodium lauroyl methyl isethionate (RCO=lauroyl, R'=$CH_3$, $M^+$=$Na^+$).

Acyl Glutamates

Where RCO=$C_6$-$C_{20}$ acyl (linear or branched, saturated or unsaturated) or mixtures thereof, R'=H or $CH_3$, $M^+$=monovalent cation, such as disodium cocoyl glutamate (RCO=coco acyl, R'=H, $M^+$=$Na^+$) and disodium lauroyl glutamate (RCO=lauroyl, R'=H, $M^+$=$Na^+$).

Acyl Aspartates

Where RCO=$C_6$-$C_{20}$ acyl (linear or branched, saturated or unsaturated) or mixtures thereof, R'=H or $CH_3$, $M^+$=monovalent cation, such as disodium N-lauroyl aspartate (RCO=lauroyl, R'=H, $M^+$=$Na^+$).

Acyl Taurates

Where RCO=$C_6$-$C_{20}$ acyl (linear or branched, saturated or unsaturated) or mixtures thereof, R'=H or $CH_3$, $M^+$=monovalent cation, such as disodium cocoyl glutamate (RCO=coco acyl, R'=H, $M^+$=$Na^+$) and disodium lauroyl glutamate (RCO=lauroyl, R'=H, $M^+$=$Na^+$).

Alkyl Phosphates

Where R=$C_6$-$C_{20}$ alkyl (linear or branched, saturated or unsaturated) or mixtures thereof and $M^+$=monovalent cation, such as potassium lauryl phosphate (R=lauryl, $C_{12}H_{25}$, $M^+$=$K^+$) and potassium C12-13 alkyl phosphate (R=$C_{12}$-$C_{13}$ alkyl, $M^+$=$K^+$)

Anionic derivatives of alkyl polyglucosides, including: sodium lauryl glucoside carboxylate, disodium coco-glucoside citrate, sodium coco-glucoside tartrate, disodium coco-glucoside sulfosuccinate; sodium cocoglucosides hydroxypropylsulfonate, sodium decylglucosides hydroxypropylsulfonate, sodium laurylglucosides hydroxypropylsulfonate; sodium hydroxypropylsulfonate cocoglucoside crosspolymer, sodium hydroxypropylsulfonate decylglucoside crosspolymer, sodium hydroxypropylsulfonate laurylglucoside crosspolymer; anionic polymeric APG derivatives, such as those described in O'Lenick, U.S. Pat. Nos. 7,507,399; 7,375,064; and 7,335,627; and combinations of two or more thereof, and the like. According to certain preferred embodiments, the non-sulfate anionic surfactants are selected from the group consisting of acyl glutamates, alpha-sulfo fatty acid esters, alpha-sulfo fatty acid salts, alpha-olefin sulfonates, and combinations of two or more thereof.

Any suitable amount of non-sulfate anionic surfactant may be used in the compositions of the present invention. In certain embodiments, the compositions comprise from greater than zero to about 25% by weight of non-sulfate anionic. In certain preferred embodiments, the compositions comprise from about 0.25 wt % to about 20 wt %, more preferable from about 0.5 wt % to about 15 wt %, still more preferably from about 1.0 wt % to about 12.5 wt %, and even more preferably from about 1.5 wt % to about 10 wt % of total non-sulfate anionic surfactants.

Any suitable ratio of wt % non-sulfate anionic surfactant to wt % zwitterionic surfactant may be used in accord with the present invention. In certain embodiments the ratio of wt % non-sulfate anionic surfactant:wt % zwitterionic surfactant is from about 0.1: to about 10:1. In certain preferred embodiments, the wt % non-sulfate anionic surfactant:wt % zwitterionic surfactant ratio is from about 0.02:1 to about 5:1, more preferably from about 0.3:1 to about 4:1. In certain more preferred embodiments, the wt. % polyglyceryl nonionic surfactant: wt % zwitterionic surfactant ratio is from about 0.5:1 to about 2:1.

In certain embodiments, the compositions of the present invention are substantially free of sulfated anionic surfactants. As used herein "substantially free of sulfated anionic surfactants" means a composition that comprises less than 1% by weight of total sulfated anionic surfactants, such as alkyl sulfates, alkyl ether sulfates, alkyl monoglyceryl ether sulfates, and the like. In preferred embodiments, compositions that are substantially free of sulfated anionic surfactants comprise less than 0.5%, more preferably less than 0.1%, and even more preferable are free of, sulfated anionic surfactants.

The compositions of the present invention may also contain any of a variety of other ingredients suitable to produce an aesthetically-desirable composition with additional functional or cosmetic benefits. Such ingredients include but are not limited to: (a) non-ethoxylated nonionic surfactants other than polyglyceryl nonionic surfactants, including but not limited to, alkyl polyglucosides (e.g. decyl glucoside, coco-glucoside, lauryl glucoside), alkyl polypentosides (e.g. caprylyl/capryl wheat bran/straw glycosides), sucrose esters (e.g. sucrose cocoate, sucrose laurate), sorbitan esters (e.g. sorbitan laurate, sorbitan caprylate), and combinations of two or more thereof and the like; (b) rheology modifiers, including but not limited to, naturally-derived polysaccharides including xanthan gum, dehydroxanthan gum, *Cyamopsis tetragonoloba* (guar) gum, *cassia* gum, *Chondrus crispus* (carrageenan) gum, alginic acid and alginate gums (e.g. algin, calcium alginate, etc.), gellan gum, pectin, microcrystalline cellulose, nonethoxylated derivatives of cellulose (e.g. sodium carboxymethylcellulose, hydroxypropyl methylcellulose, etc.), and hydroxypropyl guar, and synthetic polymers that do not comprise ethoxylated monomers or ethoxylated surfactants (e.g. as processing or dispersing aids), such as, acrylic alkali-swellable emulsion (ASE) polymers, such as Acrylates Copolymer, available under the trade name Carbopol® AQUA SF-1 from Lubrizol Corp., Brecksville, Ohio, hydrophobically-modified acrylate crosspolymers, such as Acrylates C10-30 Alkyl Acrylates Crosspolymer, available under the trade name Carbopol® 1382 from Lubrizol Corp., Brecksville, Ohio, as well as, non-ethoxylated micellar thickeners, such as: cocamide MIPA, lauryl lactyl lactate, or sorbitan sesquicaprylate, and combinations of two or more thereof and the like; (c) conditioning agents including but not limited to cationic surfactants, cationic polymers, such as, cationically-modified polysaccharides, including starch hydroxypropyltrimonium chloride, guar hydroxypropyltrimonium chloride, and hydroxypropyl guar hydroxypropyltrimonium chloride, cationic polymers derived from the (co) polymerization of ethylenically-unsaturated cationic monomers with optional hydrophilic monomers, including polyquaternium-5, polyquaternium-6, polyquaternium-7, polyquaternium-11, polyquaternium-14, polyquaternium-15, polyquaternium-28, polyquaternium-39, polyquaternium-44; polyquaternium-76; and combinations of two or more thereof, and the like; and (d) other preservatives and preservative boosters including but not limited to benzyl alcohol, caprylyl glycol, decylene glycol, ethylhexylglycerin, gluconolactone, methylisothazolinone, and combinations of two or more thereof, and the like.

In certain embodiments, the compositions produced via the present invention are preferably used as or in personal care products for treating or cleansing at least a portion of the human body. Examples of certain preferred personal care products include various products suitable for application to the skin, hair, and/or vaginal region of the body, such as shampoos, hand, face, and/or body washes, bath additives, gels, lotions, creams, and the like. As discussed above, applicants have discovered unexpectedly that the instant methods provide personal care products having reduced irritation to the skin and/or eyes and, in certain embodiments one or more of desirable properties such as foaming characteristics, rheology, and functionality, even at high surfactant concentrations.

The present invention provides methods of treating and/or cleansing the human body comprising contacting at least a portion of the body with a composition of the present invention. Certain preferred methods comprising contacting mammalian skin, hair and/or vaginal region with a composition of the present invention to cleanse such region and/or treat such region for any of a variety of conditions including, but not limited to, acne, wrinkles, dermatitis, dryness, muscle pain, itch, and the like. In certain preferred embodiments, the contacting step comprises applying a composition of the present invention to human skin, hair or vaginal region.

The cleansing methods of the present invention may further comprise any of a variety of additional, optional steps associated conventionally with cleansing hair and skin including, for example, lathering, rinsing steps, and the like.

EXAMPLES

Test methods used in the Examples are described as follows:

Zero-Shear Viscosity Test: Determinations of zero-shear apparent viscosity of the cleansing compositions were conducted on a controlled-stress rheometer (AR-2000, TA Instruments Ltd., New Castle, Del., USA). Steady-state shear stress sweeps were performed at 25.0±0.1° C. using a double-wall Couette geometry. Data acquisition and analysis were performed with the Rheology Advantage software v4.1.10 (TA Instruments Ltd., New Castle, Del., USA). Zero-shear apparent viscosities for Newtonian fluids are reported as the average of viscosity values obtained over a range of shear stresses (0.02-1.0 Pa). For pseudoplastic (shear-thinning) fluids, zero-shear apparent viscosities were calculated via the fitting of shear stress sweep data to an Ellis viscosity model.

Transepithial Permeability (TEP) Assay: Irritation to the eyes and/or skin expected for a given formulation is measured in accordance with the Invittox Protocol Number 86, the "Trans-epithelial Permeability (TEP) Assay" as set forth in Invittox Protocol Number 86 (May 1994), incorporated herein by reference. In general, the ocular and/or skin irritation potential of a product can be evaluated by determining its effect on the permeability of a cell layer, as assessed by the leakage of fluorescein through the layer. Monolayers of Madin-Darby canine kidney (MDCK) cells are grown to confluence on microporous inserts in a 24-well plate containing medium or assay buffer in the lower wells. Exposure of a layer of MDCK cells grown on a microporous membrane to a test sample is a model for the first event that occurs when an irritant comes in contact with the eye. In vivo, the outermost layers of the corneal epithelium form a selectively permeable barrier due to the presence of tight junctions between cells. On exposure to an irritant, the tight junctions separate, thereby removing the permeability barrier. Fluid is imbibed to the underlying layers of epithelium and to the stroma, causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well.

The irritation potential of a formulation is evaluated by measuring the damage to the permeability barrier in the cell monolayer following a 15 minute exposure to dilutions of the product. Barrier damage is assessed by the amount of sodium fluorescein that has leaked through to the lower well after 30 minutes, as determined spectrophotometrically. The fluorescein leakage is plotted against the concentration of test material to determine the $EC_{50}$ (the concentration of test material that causes 50% of maximum dye leakage, i.e., 50% damage to the permeability barrier). Higher scores are indicative of milder formulas.

Formulation Foam Test: The following Formulation Foam Test was performed on various cleansing compositions to determine the foam volume upon agitation according to the present invention. First, a solution of the test composition is prepared in simulated tap water. To represent the hardness of tap water, 0.36 g of calcium chloride is dissolved in 995 g of DI water. Five (5.0) grams of test composition is then added to this solution and mixed until homogeneous. To determine the Formulation Foam Volume, the test composition (1000 mL) was added to the sample tank of a SITA R-2000 foam tester (commercially available from Future Digital Scientific, Co.; Bethpage, N.Y.). The test parameters were set to repeat three runs (series count=3) of 250 ml sample size (fill volume=250 ml) with thirteen stir cycles (stir count=13) for a 15 second stir time per cycle (stir time=15 seconds) with the rotor spinning at 1200 RPM (revolution=1200) at a temperature setting of 30° C.±2° C. Foam volume data was collected at the end of each stir cycle and the average and standard deviation of the three runs was determined. The Maximum Foam Volume was reported for each Example as the value after the thirteenth stir cycle.

Clarity Test: The clarity of the cleansing compositions was determined via turbidity measurements on a HF Scientific Micro 1000 IR Turbidimeter operating at ambient temperature (22° C.±1° C.). Clarity is reported in terms of turbidity measured in nephelometric turbidity units (NTU), with clearer formulas having lower turbidity values.

Dynamic Light Scattering (DLS) Test: Dynamic light scattering (DLS, also known as Photon Correlation Spectroscopy or PCS) is a well-known method for determination of average micelle size (measured as hydrodynamic diameter, $d_H$) and micelle size distribution (A comprehensive explanation of the technique can be found in the ISO test method ISO 13321: 1996(E)). The hydrodynamic size measured by DLS is defined as the size of a hypothetical hard sphere that diffuses in the same fashion as that of the particle being measured. In practice, micellar species are dynamic (tumbling), solvated species that maybe isotropic (spherical) or anisotropic (e.g. ellipsoidal or cylindrical) in shape. Because of this, the diameter calculated from the diffusional properties of the micelle will be indicative of the apparent size of the dynamic hydrated/solvated particle; hence the terminology, "hydrodynamic diameter." Micellar solutions for determination of micelle $d_H$ are prepared by diluting the compositions to 3.0% of their original concentration with 0.1 μm-filtered deionized water, obtained from a Millipore-Q filtration system. (The target dilution of 3.0% is chosen because it is within the typical concentration range of 1.0%-10% dilution that is encountered during the use of rinse-off personal care compositions. The target dilution is also within the range of dilutions employed in the TEP test.) The samples are agitated on a vortex mixer at 1000 rpm for a minimum of five minutes and then allowed to stand overnight prior to analysis. Samples are passed through a 0.2 μm Anatop-Plus syringe filter into dust-free disposable acrylic sizing cuvettes and sealed.

The samples are analyzed using a Zetasizer Nano ZS DLS instrument (Malvern Instruments, Inc., Southborough, Mass.) operating at 25.0° C. Samples must yield a minimum count rate of 100,000 counts per second (cps) for accurate determination of micelle $d_H$ and micelle size distribution. For samples with count rates below this minimum, the sample concentration maybe be gradually increased (i.e. diluted less) until the minimum count rate is achieved. Values of micelle $d_H$ and the micelle size distribution are calculated using the Dispersion Technology Software (DTS) v4.10 package (Malvern Instruments Inc., Southborough, Mass.), which calculates the peak-average micelle $d_H$ according to the nonlinear least squares fitting method. Values of average micelle $d_H$ are reported herein as the peak-average micelle $d_H$. The reported values of micelle $d_H$ are the average of three individual measurement runs.

Additives exhibiting relatively large values of $d_H$ (i.e. greater than about 200 nm) compared to micellar species, for example, high MW polymeric rheology modifiers, polymeric conditioners, particulate opacifiers, (micro)emulsions of hydrophobic emollients, silicone (micro)emulsions, etc., are routinely added to cleansing compositions comprising micellar species. To those skilled in the art of DLS, it is apparent that such nonmicellar materials will exhibit light scattering intensities orders of magnitude greater than the relatively smaller micellar species in the diluted sample. The scattering intensity of such materials will overwhelm the scattering signal of the micellar species, thus interfering in the accurate determination of micelle $d_H$. Typically, this type of interference will lead to an erroneously large measured value of micelle $d_H$. To avoid such interference, it is most preferable to measure the micelle $d_H$ of the composition in the absence of additives exhibiting values of $d_H$ greater than about 200 nm. Those skilled in the art of DLS will recognize that additives exhibiting large values of $d_H$ should be separated from the sample via filtration or ultracentrifugation prior to determination of the micelle $d_H$ of the sample. Alternatively, higher order analysis of the DLS data using the Dispersion Technology Software v4.10 package may also be employed to obtain enhanced resolution and properly characterize micelle $d_H$ in the presence of nonmicellar scattering species.

Example 1

Preparation and Measurement of Certain Compositions of the Invention (E1-E9)

Compositions E1-E9 were made in accord with the following procedure: Unless otherwise indicated, all materials were added in the weight percent amounts as indicated for each composition in Tables 1 and 2, and the particular polyglyceryl nonionic, zwitterionic, and anionic surfactants used for each composition were those also indicated in Tables 1 and 2. To an appropriately sized vessel equipped with a hotplate and overhead mechanical stirrer, 60 parts water, sodium benzoate, and sodium chloride (if any) were added. While mixing at 200-250 rpm and heating to 40-50° C., the polyglyceryl nonionic surfactant(s) was (were) added. The zwitterionic and anionic surfactants were added, and the batch was allowed to mix at 40-50° C. until uniform. The batch was allowed to mix while cooling to below 30° C. and was then adjusted to the desired pH value (pH=4.5-4.9 using necessary amount of citric acid and/or sodium hydroxide solutions (20% w/w). Water was added in q.s. to 100 wt %, and the batch is allowed to mix until uniform before being discharged to an appropriate storage vessel.

The Zero Shear Viscosity, Max. Foam Volume, Turbidity, TEP, and Average Micelle size were measured for E1-E9 in accord with the Zero Shear Viscosity Test, Formulation Foam Test, Clarity Test, TEP Test and DLS Test, respectively, as described herein. The results are shown in Table 3.

TABLE 1

| INCI name | Trade Name | Activity (%) | E1 wt. % | E2 wt. % | E3 wt. % | E4 wt. % | E5 wt. % |
|---|---|---|---|---|---|---|---|
| Polyglyceryl nonionic | | | | | | | |
| Polyglyceryl-10 Oleate | Polyaldo 10-1-O (Lonza) | 100 | 3.60 | 3.60 | 3.60 | — | 3.60 |
| Polyglyceryl-10 Laurate | Polyaldo 10-1-L (Lonza) | 100 | — | 1.00 | 1.00 | 3.60 | — |
| Zwitterionic | | | | | | | |
| Coco-Betaine | Dehyton AB-30 (Cognis) | 30 | 12.50 | 18.77 | 18.77 | 12.50 | — |
| Lauryl Hydroxysultaine | Mackam LHS (Rhodia-McIntyre) | 42 | — | — | — | — | 8.93 |
| Anionic | | | | | | | |
| Sodium Cocoyl Glutamate | Plantapon ACG HC (Cognis) | 42 | 6.44 | 9.64 | — | — | 6.43 |
| Sodium Methyl 2-Sulfolaurate (and) Disodium 2-Sulfolaurate | Alpha-Step PC-48 (Stepan) | 38 | — | — | 10.66 | 7.11 | — |
| Organic acids | | | | | | | |
| Sodium Benzoate | Sodium Benzoate, NF, FCC | 100 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.9 | Q.S. to pH 4.9 | Q.S. to pH 4.5 |
| Other | | | | | | | |
| Sodium Choride | Sodium Choride, USP | 100 | — | 4.00 | — | — | — |
| Water | Purified water, USP | 100 | Q.S. to 100% | Q.S. to 100% | Q.S. to 100% | Q.S. to 100% | Q.S. to 100% |

TABLE 2

| INCI name | Trade Name | Activity (%) | E6 wt. % | E7 wt. % | E8 wt. % | E9 wt. % |
|---|---|---|---|---|---|---|
| Polyglyceryl nonionic | | | | | | |
| Polyglyceryl-10 Oleate | Polyaldo 10-1-O (Lonza) | 100 | 3.60 | 3.60 | 3.60 | 3.60 |
| Polyglyceryl-10 Laurate | Polyaldo 10-1-L (Lonza) | 100 | 1.00 | 1.00 | 1.00 | — |
| Polyglyceryl-10 Lauryl Ether | PGLAL ML 10 (Daicel) | 100 | — | — | — | 1.00 |
| Zwitterionic | | | | | | |
| Lauryl Hydroxysultaine | Mackam LHS (Rhodia-McIntyre) | 42 | 13.40 | — | — | — |
| Sodium Lauroampho-hydroxypropylsulfonate | Mackam LS (Rhodia-McIntyre) | 35 | — | 16.08 | 16.08 | 16.08 |
| Anionic | | | | | | |
| Sodium Cocoyl Glutamate | Plantapon ACG HC (Cognis) | 42 | 9.64 | 9.64 | — | 9.64 |
| Sodium Methyl 2-Sulfolaurate (and) Disodium 2-Sulfolaurate | Alpha-Step PC-48 (Stepan) | 38 | — | 10.66 | — | — |

TABLE 2-continued

| INCI name | Trade Name | Activity (%) | E6 wt. % | E7 wt. % | E8 wt. % | E9 wt. % |
|---|---|---|---|---|---|---|
| Organic Acids | | | | | | |
| Sodium Benzoate | Sodium Benzoate, NF, FCC | 100 | 0.50 | 0.50 | 0.50 | 0.50 |
| Citric Acid | Citric Acid solution | 20 | Q.S. to pH 4.5 | Q.S. to pH 4.9 | Q.S. to pH 4.5 | Q.S. to pH 4.5 |
| Other | | | | | | |
| Water | Purified water, USP | 100 | Q.S. to 100% | Q.S. to 100% | Q.S. to 100% | Q.S. to 100% |

TABLE 3

| | Zero Shear Viscosity (cP) | Max. Foam Vol. (mL) | Turbidity (IR, NTU) | TEP EC$_{50}$ value (%) | Average Micelle d$_H$ (nm) |
|---|---|---|---|---|---|
| E1 | 219 | 512 ± 6 | 9.0 | 4.73 ± 1.91 | 20.5 |
| E2 | 295 | 746 ± 12 | 5.7 | 3.63 ± 1.71 | 14.1 |
| E3 | 488 | 830 ± 1 | 4.8 | 3.18 ± 0.91 | 6.6 |
| E4 | 582 | 830 ± 6 | 9.7 | 3.32 ± 0.40 | 6.5 |
| E5 | 273 | 584 ± 7 | 8.8 | 4.26 ± 1.70 | 14.4 |
| E6 | 253 | 793 ± 5 | 7.8 | 2.97 ± 0.26 | 10.9 |
| E7 | 434 | 841 ± 7 | 7.5 | 2.22 ± 0.26 | 8.0 |
| E8 | 548 | 799 ± 4 | 12.8 | 4.61 ± 0.90 | 15.4 |
| E9 | 305 | 776 ± 9 | 7.4 | 3.68 ± 0.35 | 12.1 |

Example 2

Preparation and Measurement of Certain Compositions of the Invention (E10-E11)

Compositions E10 and E11 were made in accord with the procedure of Example 1, with the additional steps of adding the glycerin with the water and sodium benzoate, and adding any nonionic surfactant (e.g. Coco-Glucoside for E11) with the zwitterionic and anionic surfactants. The materials and amounts for E10 and E11 are shown in Table 4. The Zero Shear Viscosity, Max. Foam Volume, Turbidity, TEP, and Average Micelle size were measured as above and reported in Table 5.

TABLE 4

| INCI name | Trade Name | Activity (%) | E10 wt. % | E11 wt. % |
|---|---|---|---|---|
| Polyglyceryl nonionic | | | | |
| Polyglyceryl-10 Laurate | Polyaldo 10-1-L (Lonza) | 100 | 1.00 | 1.00 |
| Zwitterionic | | | | |
| Cocamidopropyl-Betaine | Tegobetaine L7-V (Evonik) | 30 | 10.00 | 10.00 |
| Anionic | | | | |
| Sodium C14-C16 Olefin Sulfonate | Bioterge AS-90 (Stepan) | 85 | 2.20 | 2.20 |
| Organic Acids | | | | |
| Sodium Benzoate | Sodium Benzoate, NF, FCC | 100 | 0.50 | 0.50 |
| Citric Acid | Citric Acid solution | 20 | Q.S. to pH 4.5 | Q.S. to pH 4.5 |

TABLE 4-continued

| INCI name | Trade Name | Activity (%) | E10 wt. % | E11 wt. % |
|---|---|---|---|---|
| Other | | | | |
| Coco-Glucoside | Plantacare 818 NP (Cognis) | 52 | — | 6.00 |
| Glycerin | Glycerin, USP | 100 | 0.50 | 0.50 |
| Sodium Choride | Sodium Choride, USP | 100 | 2.40 | 0.40 |
| Water | Purified water, USP | 100 | Q.S. to 100% | Q.S. to 100% |

TABLE 5

| | Zero Shear Viscosity (cP) | Max. Foam Vol. (mL) | Turbidity (IR, NTU) | TEP EC$_{50}$ value (%) | Average Micelle d$_H$ (nm) |
|---|---|---|---|---|---|
| E10 | 1519 | 609 ± 10 | 16.5 | 3.38 ± 0.71 | 10.3 |
| E11 | 844 | 828 ± 6 | 14.6 | 3.76 ± 0.58 | 9.4 |

Example 3

Preparation and Measurement of Comparative Compositions (C1-C3)

Comparative compositions C1-C3 were made in accord with the procedure of Example 2, except that no polyglyceryl nonionic surfactant is added. The materials and amounts for C1-C3 are shown in Table 6. The TEP and Average Micelle size were measured as above and reported in Table 7. Applicants note the comparative examples are normalized to the same surfactant concentrations (wt %) as corresponding Inventive Examples (e.g. C1 corresponds to E2 without polyglyceryl nonionics and normalized to equivalent surfactant concentration (14.28 wt % active); C2 similarly corresponds to E3; and C3 corresponds to E2 with alkyl polyglucoside nonionics substituted for polyglyceryl nonionics).

TABLE 6

| INCI name | Trade Name | Activity (%) | C1 wt. % | C2 wt. % | C3 wt. % |
|---|---|---|---|---|---|
| Zwitterionic | | | | | |
| Coco-Betaine | Dehyton AB-30 (Cognis) | 30 | 27.67 | 27.67 | 18.77 |

TABLE 6-continued

| INCI name | Trade Name | Activity (%) | C1 wt. % | C2 wt. % | C3 wt. % |
|---|---|---|---|---|---|
| Anionic | | | | | |
| Sodium Cocoyl Glutamate | Plantapon ACG HC (Cognis) | 42 | 14.24 | — | 9.64 |
| Sodium Methyl 2-Sulfolaurate (and) Disodium 2-Sulfolaurate | Alpha-Step PC-48 (Stepan) | 38 | — | 15.74 | — |
| Organic Acids | | | | | |
| Sodium Benzoate | Sodium Benzoate, NF, FCC | 100 | 0.50 | 0.50 | 0.50 |
| Citric Acid | Citric Acid solution | 20 | Q.S. to pH 4.5 | Q.S. to pH 4.8 | Q.S. to pH 4.5 |
| Other | | | | | |
| Coco Glucoside | Plantacare 818 NP (Cognis) | 52 | — | — | 6.92 |
| Decyl Glucoside | Plantaren 2000N UP (Cognis) | 52 | — | — | 1.92 |
| Sodium Choride | Sodium Choride, USP | 100 | 4.00 | — | — |
| Water | Purified water, USP | 100 | Q.S. to 100% | Q.S. to 100% | Q.S. to 100% |

TABLE 7

| | TEP EC$_{50}$ value (%) | Average Micelle d$_H$ (nm) |
|---|---|---|
| C1 | 1.34 ± 0.20 | 10.1 |
| C2 | 3.36 ± 0.25 | 5.8 |
| C3 | 2.42 ± 0.14 | 17.5 |

Example 4

Preparation and Measurement of Comparative Compositions (C4 and C5)

Comparative compositions C4 and C5 as shown in Table 8 correspond to, and were made in accord with the procedure for, Examples 1 and 3 respectively, in U.S. Pat. No. 5,478,490 issued to Russo et al, except that the pH of the compositions was lowered to 4.5 with citric acid. Applicants discovered that when prepared at such relatively low pH values, C4 and C5 were both opaque (Turbidity of greater than 100 per the Clarity Test) and unstable (the compositions phase separated upon standing overnight).

TABLE 8

| INCI name | Trade Name | Activity (%) | C4 wt. % | C5 wt. % |
|---|---|---|---|---|
| Polyglyceryl nonionic | | | | |
| Polyglyceryl-10 Oleate | Polyaldo 10-1-O (Lonza) | 100 | 1.50 | 1.50 |
| Zwitterionic | | | | |
| Cocamidopropyl Betaine | Tegobetaine L7-V (Evoink) | 30 | 10.00 | 10.00 |
| Sodium Cocoamphoacetate | Amphoterge W (Lonza) | 40 | 2.00 | 3.00 |
| Disodium Cocoamphodiacetate | Amphoterge W-2 (Lonza) | 40 | 2.00 | 3.00 |
| Anionic | | | | |
| Sodium Lauryl Sulfate | Stepanol WA-EXTRA (Stepan) | 30 | 6.00 | 5.00 |
| Organic Acids | | | | |
| Citric Acid | Citric Acid solution | 20 | Q.S. to pH 4.5 | Q.S. to pH 4.5 |
| Other | | | | |
| DMDM Hydantoin (and) Iodopropynyl Butylcarbamate | Glydant Plus | 100 | 0.05 | 0.05 |
| Glycerin | Glycerin, USP | 100 | 2.50 | 2.50 |
| Fragrance | Fragrance TA H23194/01 (Givaudan) | 100 | 0.50 | 0.50 |
| Water | Purified water, USP | 100 | Q.S. to 100% | Q.S. to 100% |

Example 5

Preparation and Measurement of Comparative Compositions (C6-C9)

Comparative compositions C6-C9 were made in accord with the procedure of Example 1. The materials and amounts for C6-C9 are shown in Table 9. Compositions C6-C9 were tested in accord with the Clarity Test and all four compositions exhibited a turbidity of >100 (opaque).

TABLE 9

| INCI name | Trade Name | Activity (%) | C6 wt. % | C7 wt. % | C8 wt. % | C9 wt. % |
|---|---|---|---|---|---|---|
| Polyglyceryl nonionic | | | | | | |
| Polyglyceryl-10 Oleate | Polyaldo 10-1-O (Lonza) | 100 | 3.60 | 3.60 | 3.60 | 3.60 |
| Zwitterionic | | | | | | |
| Coco-Betaine | Dehyton AB-30 (Cognis) | 30 | 12.50 | 12.50 | 12.50 | 12.50 |
| Anionic | | | | | | |
| Sodium Cocoyl Sarcosinate | Hamposyl C-30 (Chattem) | 30 | 9.00 | — | — | — |
| Disodium Lauryl Sulfosuccinate | Mackanate LO (McIntyre) | 40 | — | 6.75 | — | — |

TABLE 9-continued

| INCI name | Trade Name | Activity (%) | C6 wt. % | C7 wt. % | C8 wt. % | C9 wt. % |
|---|---|---|---|---|---|---|
| Sodium Methyl 2-Sulfolaurate (and) Disodium 2-Sulfolaurate (and) Sodium Lauryl Sulfoacetate | Stepan Mild PCL (Stepan) | 23 | — | — | 11.54 | — |
| Sodium Lauroyl Lactylate | Stepan SLL-FB (Stepan) | 100 | — | — | — | 2.70 |
| Organic Acids | | | | | | |
| Sodium Benzoate | Sodium Benzoate, NF, FCC | 100 | 0.50 | 0.50 | 0.50 | 0.50 |
| Citric Acid | Citric Acid solution | 20 | Q.S. to pH 4.5 | Q.S. to pH 4.5 | Q.S. to pH 4.9 | Q.S. to pH 4.9 |
| Other | | | | | | |
| Water | Purified water, USP | 100 | Q.S. to 100% | Q.S. to 100% | Q.S. to 100% | Q.S. to 100% |

Example 6

Measurement of Zero-Shear Viscosity and pH

Figure 1:
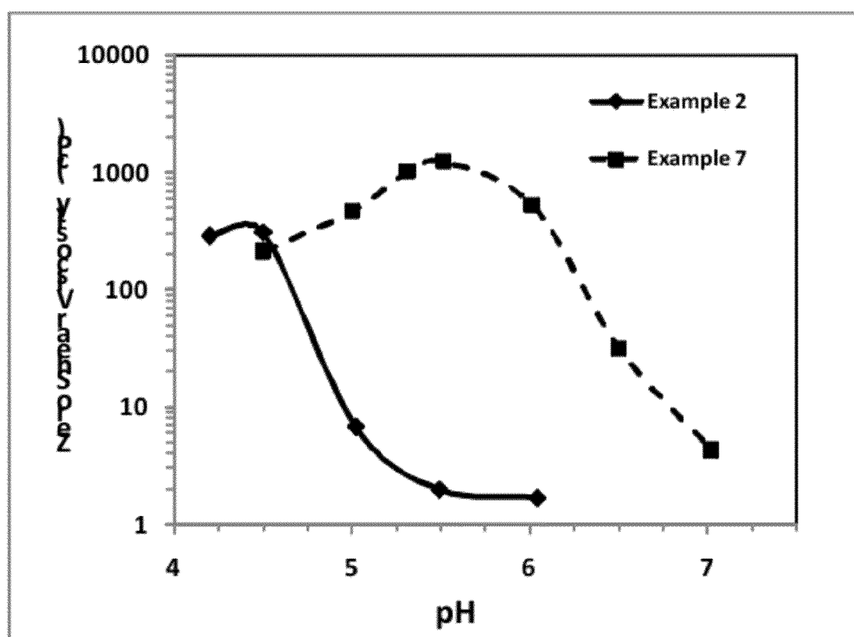
FIG. 1 is a graphical depiction of the Zero-Shear Viscosity as a function of pH for certain compositions of the claimed invention.

The Zero-Shear Viscosity as a function of pH was measured for E2 and E7 in accord with the Zero-Shear Viscosity Test. E2 and E7 were prepared and the pH measured. The pH for each was lowered using citric acid and Zero-Shear Viscosity and pH measured again. This was repeated as shown in FIG. 1. As a result, applicants discovered that improved viscosity was realized at relatively low pH for the compositions.

What is claimed is:

1. A composition comprising a polyglyceryl nonionic surfactant, a zwitterionic surfactant, an organic acid preservative, water, and a non-sulfate anionic surfactant selected from the group consisting of acyl aspartates, acyl glutamates, acyl isethionates, acyl taurates, alpha-sulfo fatty acid esters, alpha-sulfo fatty acid salts, alpha-olefin sulfonates, alkyl sulfonates, alkyl phosphates, anionic derivatives of alkyl polyglucosides, and combinations of two or more thereof, wherein the composition is substantially free of ethoxylated materials and has a pH of 5.4 or less.

2. The composition of claim 1 wherein said polyglyceryl nonionic surfactant comprises a compound selected from the group consisting of polyglyceryl esters, polyglyceryl ethers, polyglyceryl sorbitan fatty acid esters, and combinations of two or more thereof.

3. The composition of claim 1 wherein said polyglyceryl nonionic surfactant comprises a compound selected from the group consisting of polyglyceryl-4 caprylate/caprate, polyglyceryl-5 caprylate/caprate, polyglyceryl-6 caprylate/caprate, polyglyceryl-7 caprylate/caprate, polyglyceryl-8 caprylate/caprate, polyglyceryl-9 caprylate/caprate, polyglyceryl-10 caprylate/caprate, polyglyceryl-4 caprate, polyglyceryl-5 caprate, polyglyceryl-6 caprate, polyglyceryl-7 caprate, polyglyceryl-8 caprate, polyglyceryl-9 caprate, polyglyceryl-10 caprate, polyglyceryl-4 laurate, polyglyceryl-5 laurate, polyglyceryl-6 laurate, polyglyceryl-7 laurate, polyglyceryl-8 laurate, polyglyceryl-9 laurate, polyglyceryl-10 laurate, polyglyceryl-6 cocoate, polyglyceryl-7 cocoate, polyglyceryl-8 cocoate, polyglyceryl-9 cocoate, polyglyceryl-10 cocoate, polyglyceryl-11 cocoate, polyglyceryl-12 cocoate, polyglyceryl-6 myristate, polyglyceryl-7 myristate, polyglyceryl-8 myristate, polyglyceryl-9 myristate, polyglyceryl-10 myristate, polyglyceryl-11 myristate, polyglyceryl-12 myristate, polyglyceryl-10 oleate, polyglyceryl-11 oleate, polyglyceryl-12 oleate, polyglyceryl-10 stearate, polyglyceryl-11 stearate, polyglyceryl-12 stearate, and combinations of two or more thereof.

4. The composition of claim 1 wherein said polyglyceryl nonionic surfactant has a DP of about 6 to about 20.

5. The composition of claim 1 wherein said zwitterionic surfactant is selected from the group consisting of alkyl betaines, alkyl hydroxysultaines, alkylamidoalkyl betaines, alkylamidoalkyl hydroxysultaines, amphohydroxypropylsulfonates, and combinations of two or more thereof.

6. The composition of claim 1 comprising a ratio of wt % polyglyceryl nonionic surfactant:wt % zwitterionic surfactant of from about 0.05:1 to about 3:1.

7. The composition of claim 1 wherein said organic acid comprises benzoic acid, sorbic acid, p-anisic acid or a combination thereof.

8. The composition of claim 1 comprising a ratio of wt % non-sulfate anionic surfactant:wt % zwitterionic surfactant of from about 0.3:1 to about 4:1.

9. A personal care product suitable for application to the skin, hair, and/or vaginal region of the body comprising a composition of claim 1, said product being in the form of a shampoo, wash, bath additive, gel, lotion, or cream.

10. The personal care product of claim 9 wherein said polyglyceryl nonionic surfactant comprises a compound selected from the group consisting of polyglyceryl-4 caprylate/caprate, polyglyceryl-5 caprylate/caprate, polyglyceryl-6 caprylate/caprate, polyglyceryl-7 caprylate/caprate, polyglyceryl-8 caprylate/caprate, polyglyceryl-9 caprylate/caprate, polyglyceryl-10 caprylate/caprate, polyglyceryl-4 caprate, polyglyceryl-5 caprate, polyglyceryl-6 caprate, polyglyceryl-7 caprate, polyglyceryl-8 caprate, polyglyceryl-9 caprate, polyglyceryl-10 caprate, polyglyceryl-4 laurate, polyglyceryl-5 laurate, polyglyceryl-6 laurate, polyglyceryl-7 laurate, polyglyceryl-8 laurate, polyglyceryl-9 laurate, polyglyceryl-10 laurate, polyglyceryl-6 cocoate, polyglyceryl-7 cocoate, polyglyceryl-8 cocoate, polyglyceryl-9 cocoate, polyglyceryl-10 cocoate, polyglyceryl-11 cocoate, polyglyceryl-12 cocoate, polyglyceryl-6 myristate, polyglyceryl-7 myristate, polyglyceryl-8 myristate, polyglyceryl-9 myristate, polyglyceryl-10 myristate, polyglyceryl-11 myristate, polyglyceryl-12 myristate, polyglyceryl-10 oleate, polyglyceryl-11 oleate, polyglyceryl-12 oleate, polyglyceryl-10 stearate, polyglyceryl-11 stearate, polyglyceryl-12 stearate, and combinations of two or more thereof, said zwitterionic surfactant is selected from the group consisting of alkyl betaines, alkyl hydroxysultaines, alkylamidoalkyl betaines, alkylamidoalkyl hydroxysultaines, ampho-hydroxypropylsulfonates, and combinations of two or more thereof, said non-sulfate anionic surfactant is selected from the group consisting of acyl glutamates, alpha-sulfo fatty acid esters, alpha-sulfo fatty acid salts, alpha-olefin sulfonates, and combinations of two or more thereof, and said organic acid comprises sodium benzoate, potassium sorbate, or a combination thereof.

11. A composition comprising a polyglyceryl nonionic surfactant, a zwitterionic surfactant, an organic acid preservative, and water, wherein the composition is substantially free of ethoxylated materials, substantially free of sulfated anionic surfactants, and has a pH of about 5.4 or less.

12. The composition of claim 11 wherein said polyglyceryl nonionic surfactant comprises a compound selected from the group consisting of polyglyceryl esters, polyglyceryl ethers, polyglyceryl sorbitan fatty acid esters, and combinations of two or more thereof.

13. The composition of claim 11 wherein said polyglyceryl nonionic surfactant comprises a compound selected from the group consisting of polyglyceryl-4 caprylate/caprate, polyglyceryl-5 caprylate/caprate, polyglyceryl-6 caprylate/caprate, polyglyceryl-7 caprylate/caprate, polyglyceryl-8 caprylate/caprate, polyglyceryl-9 caprylate/caprate, polyglyceryl-10 caprylate/caprate, polyglyceryl-4 caprate, polyglyceryl-5 caprate, polyglyceryl-6 caprate, polyglyceryl-7 caprate, polyglyceryl-8 caprate, polyglyceryl-9 caprate, polyglyceryl-10 caprate, polyglyceryl-4 laurate, polyglyceryl-5 laurate, polyglyceryl-6 laurate, polyglyceryl-7 laurate, polyglyceryl-8 laurate, polyglyceryl-9 laurate, polyglyceryl-10 laurate, polyglyceryl-6 cocoate, polyglyceryl-7 cocoate, polyglyceryl-8 cocoate, polyglyceryl-9 cocoate, polyglyceryl-10 cocoate, polyglyceryl-11 cocoate, polyglyceryl-12 cocoate, polyglyceryl-6 myristate, polyglyceryl-7 myristate, polyglyceryl-8 myristate, polyglyceryl-9 myristate, polyglyceryl-10 myristate, polyglyceryl-11 myristate, polyglyceryl-12 myristate, polyglyceryl-10 oleate, polyglyceryl-11 oleate, polyglyceryl-12 oleate, polyglyceryl-10 stearate, polyglyceryl-11 stearate, polyglyceryl-12 stearate, and combinations of two or more thereof.

14. The composition of claim 11 wherein said polyglyceryl nonionic surfactant has a DP of about 6 to about 20.

15. The composition of claim 11 wherein said zwitterionic surfactant is selected from the group consisting of alkyl betaines, alkyl hydroxysultaines, alkylamidoalkyl betaines, alkylamidoalkyl hydroxysultaines, amphohydroxypropylsulfonates, and combinations of two or more thereof.

16. The composition of claim 11 comprising a ratio of wt % polyglyceryl nonionic surfactant:wt % zwitterionic surfactant of from about 0.025:1 to about 4:1.

17. The composition of claim 11 wherein said organic acid comprises benzoic acid, sorbic acid, p-anisic acid, or a combination thereof.

18. A personal care product suitable for application to the skin, hair, and/or vaginal region of the body comprising a composition of claim 11, said product being in the form of a shampoo, wash, bath additive, gel, lotion, or cream.

19. The personal care product of claim 18 wherein said polyglyceryl nonionic surfactant comprises a compound selected from the group consisting of polyglyceryl-4 caprylate/caprate, polyglyceryl-5 caprylate/caprate, polyglyceryl-6 caprylate/caprate, polyglyceryl-7 caprylate/caprate, polyglyceryl-8 caprylate/caprate, polyglyceryl-9 caprylate/caprate, polyglyceryl-10 caprylate/caprate, polyglyceryl-4 caprate, polyglyceryl-5 caprate, polyglyceryl-6 caprate, polyglyceryl-7 caprate, polyglyceryl-8 caprate, polyglyceryl-9 caprate, polyglyceryl-10 caprate, polyglyceryl-4 laurate, polyglyceryl-5 laurate, polyglyceryl-6 laurate, polyglyceryl-7 laurate, polyglyceryl-8 laurate, polyglyceryl-9 laurate, polyglyceryl-10 laurate, polyglyceryl-6 cocoate, polyglyceryl-7 cocoate, polyglyceryl-8 cocoate, polyglyceryl-9 cocoate, polyglyceryl-10 cocoate, polyglyceryl-11 cocoate, polyglyceryl-12 cocoate, polyglyceryl-6 myristate, polyglyceryl-7 myristate, polyglyceryl-8 myristate, polyglyceryl-9 myristate, polyglyceryl-10 myristate, polyglyceryl-11 myristate, polyglyceryl-12 myristate, polyglyceryl-10 oleate, polyglyceryl-11 oleate, polyglyceryl-12 oleate, polyglyceryl-10 stearate, polyglyceryl-11 stearate, polyglyceryl-12 stearate, and combinations of two or more thereof, said zwitterionic surfactant is selected from the group consisting of alkyl betaines, alkyl hydroxysultaines, alkylamidoalkyl betaines, alkylamidoalkyl hydroxysultaines, ampho-hydroxypropylsulfonates, and combinations of two or more thereof, said organic acid comprises sodium benzoate, potassium sorbate, or a combination thereof, and said composition further comprises a non-sulfate anionic surfactant selected from the group consisting of acyl glutamates, alpha-sulfo fatty acid esters, alpha-sulfo fatty acid salts, alpha-olefin sulfonates, and combinations of two or more thereof.

20. A method of cleansing the human body comprising the step of applying to at least a portion of the human body, a composition of claim 1.

21. A method of cleansing the human body comprising the step of applying to at least a portion of the human body, a composition of claim 19.

* * * * *